United States Patent
Zweymüller (10) Patent No.: US 7,497,875 B1
(45) Date of Patent: Mar. 3, 2009

(54) FLAT SHAFT OF A HIP-JOINT PROSTHESIS FOR ANCHORING IN THE FEMUR

(75) Inventor: Karl Zweymüller, Vienna (AT)

(73) Assignee: Smith & Nephew Orthopaedics AG, Rotkreuz (CH)

( * ) Notice: Subject to any disclaimer, the term of this patent is extended or adjusted under 35 U.S.C. 154(b) by 0 days.

(21) Appl. No.: 09/958,463

(22) PCT Filed: Apr. 7, 2000

(86) PCT No.: PCT/EP00/03143

§ 371 (c)(1),
(2), (4) Date: Apr. 9, 2002

(87) PCT Pub. No.: WO00/59410

PCT Pub. Date: Oct. 12, 2000

(30) Foreign Application Priority Data

Apr. 7, 1999 (DE) .................. 199 15 677
Jun. 23, 1999 (DE) .................. 199 28 790

(51) Int. Cl.
*A61F 2/36* (2006.01)

(52) U.S. Cl. .................. 623/23.35; 623/23.24

(58) Field of Classification Search ............ 623/23.35, 623/23.24, 23.28, 23.15, 23.18, 23.19, 23.31, 623/23.11, 23.14, 23.26, 23.29, 22.43, 22.46
See application file for complete search history.

(56) References Cited

U.S. PATENT DOCUMENTS

| | | | | |
|---|---|---|---|---|
| 3,067,740 A | * | 12/1962 | Haboush | 623/22.15 |
| 4,359,785 A | * | 11/1982 | Niederer | 623/23.15 |
| 4,661,112 A | * | 4/1987 | Muller | 623/23.22 |
| 4,728,334 A | * | 3/1988 | Spotorno | 623/23.31 |
| 4,846,393 A | * | 7/1989 | Devillard | 228/178 |
| 4,865,608 A | * | 9/1989 | Brooker, Jr. | 623/23.29 |
| 4,979,958 A | * | 12/1990 | Niwa et al. | 623/23.29 |
| 5,456,717 A | * | 10/1995 | Zweymuller et al. | 623/8 |
| 5,480,452 A | * | 1/1996 | Hofmann et al. | 623/23.28 |
| 5,507,833 A | * | 4/1996 | Bohn | 623/23.3 |

(Continued)

FOREIGN PATENT DOCUMENTS

AT    391 264 B    9/1990

(Continued)

OTHER PUBLICATIONS

Bohm, G., Lintner, F., Auterith, A., Lester D.K., Zweymuller, K., *Morphometric Examination of Straight, Tapered Titanium Stems*, Clinical Orthopaedics and Related Research, 2001, pp. 13-24, No. 393, Lippincott Williams & Wilkins, Inc.

(Continued)

*Primary Examiner*—Pedro Philogene
(74) *Attorney, Agent, or Firm*—Knobbe, Martens, Olson & Bear LLP (57) ABSTRACT

A flat shaft of a hip-joint prosthesis for anchoring in a femur. The shaft expands on all sides towards a proximal end from a distal end of the shaft and medially merges with a curved section that is continuous with a prosthesis neck. The shaft is additionally expanded in a proximal region along a proximal direction on at least one of an anterior and posterior surfaces.

52 Claims, 7 Drawing Sheets

U.S. PATENT DOCUMENTS

| | | | |
|---|---|---|---|
| 5,593,451 A * | 1/1997 | Averill et al. | 623/23.15 |
| 5,665,090 A | 9/1997 | Rockwood et al. | |
| 5,725,586 A * | 3/1998 | Sommerich | 623/23.35 |
| 5,755,811 A * | 5/1998 | Tanamal et al. | 623/23.35 |
| 5,928,289 A * | 7/1999 | Deckner | 623/23.15 |
| 6,436,148 B1 * | 8/2002 | DeCarlo et al. | 623/23.15 |
| 6,540,788 B1 * | 4/2003 | Zweymuller | 623/23.24 |
| 6,808,539 B2 * | 10/2004 | Zweymuller | 623/23.24 |
| 2006/0206212 A1 | 9/2006 | Zweymuller | |
| 2006/0276904 A1 | 12/2006 | Zweymuller | |

FOREIGN PATENT DOCUMENTS

| | | | | |
|---|---|---|---|---|
| DE | 2805 305 C2 | 3/1989 | | |
| DE | 295 80 466 U1 | 11/1996 | | |
| EP | 0 032 165 B1 | 12/1983 | | |
| EP | 0 720 839 A1 | 12/1995 | | |
| EP | 0 700 670 A1 | 3/1996 | | |
| EP | 0700670 A1 * | 3/1996 | | 623/23.35 |
| FR | 2 634 642 A1 | 8/1988 | | |
| FR | 2 639 821 A1 | 12/1988 | | |
| FR | 2 634 642 | 2/1990 | | |

OTHER PUBLICATIONS

Clements, J.P., Gheduzzi, S., Zweymuller, K., Lintner F., Schmotzer, H. Learmonth, I.D., Miles, A.W., *An In Vitro Cadaveric Biomechanical Evaluation of a Cementless Hip stem Comparison of Long and Short Term Stability*, 51$^{st}$ Annual Meeting of the Orthopaedic Research Society, 2005, Paper No. 0266, Centre for Orthopaedic Biomechanics, University of Bath, UK.

Osteonics Brochure for Omniflex-Ha™ Total Hip System, 1991, 8 pages.

Depuy, Inc. Brochure for the AML™ Femoral Component with Porocoat®, 1983, 2 pages.

Operating Technique Manual for the AML™ Total Hip System, available before Apr. 9, 2002, 32 pages.

Slide Presentation with Hip Stem Designs Available Before Apr. 9, 2002, 2 pages.

Office Action in U.S. Appl. No. 11/432,914, mailed Aug. 22, 2007.

Office Action in U.S. Appl. No. 11/433,067, mailed Oct. 22, 2007.

* cited by examiner

FLAT SHAFT OF A HIP-JOINT PROSTHESIS FOR ANCHORING IN THE FEMUR

BACKGROUND OF THE INVENTION

1. Field of the Invention

The invention relates to a flat shaft of a hip-joint prosthesis for anchoring in the femur according to the precharacterizing clause of claim 1.

2. Description of the Related Art

A shaft of this kind is known from the patent EP 0 032 165 B1. In this known construction the shaft is approximately conically tapered, expanding on all sides from the distal end toward the proximal end, into a region situated at about ⅔ and ¾ of the length of the shaft as measured on its long axis. On the medial narrow side, the conical part of the shaft merges with a continuously curving arch that ends in a collar-like projection. This projection separates a femur-anchoring section of the shaft from a prosthesis neck comprising a peg that tapers conically towards its proximal end, which serves to receive a spherical joint head. The axis of the prosthesis neck intersects the long axis of the shaft at an angle that corresponds substantially to the angle between the neck and axis of the femur in a natural hip joint.

The known construction has proved valuable in that it avoids a so-called "closure rotation" that occurs when the prosthesis is inserted, and does not require the plane of resection to be positioned too low on the neck of the femur. This disadvantagous "closure rotation" is brought about as follows: the blade of the conventional prosthesis shafts must have a certain minimal thickness, so that when such a shaft is completely inserted, it often rotates within the femoral bone because the multiple curvatures of the proximal end of the femur cause a straight or even slightly curved object to be deflected by the wall of the bone.

SUMMARY OF THE INVENTION

It is the objective of the present invention to disclose an improved shaft of this generic kind that can be better anchored, in particular in the proximal region.

This objective is achieved by a flat shaft with the characteristics given in claim 1.

The invention includes the idea that in its proximal region the shaft is slightly overdimensioned in comparison to the so-called "rasped" or "null" dimension (that of the cavity prepared in the femur to accommodate the shaft), with respect to its anterior-posterior extent as well as, where appropriate, its medial-lateral extent, whereas in the middle and distal sections it is constructed so as to match substantially exactly the dimensions of the rasped marrow cavity. As a result of this feature, the spongiosa can be compressed by a specified amount, with respect to both area and volume, so that to some extent a press-fitting of the shaft is achieved in the proximal region of the femur. This kind of compression is substantially less critical that that produced by known arrangements with proximal ribs that cut into the femur and generate high peak tensions, which involve the risk of splitting the bone. The presence of a gap between the shaft and the rasped cavity is avoided, while at the same time in the distal region it is possible to rasp precisely against/into the cortical substance of the bone.

An advantageous implementation of this idea consists in providing an extra expansion or thickening, in addition to the customary "conical" expansion, in the proximal end region of the shaft on at least one of its flat sides.

This structural feature improves the seating of the shaft in the proximal region of the femur without introducing the risk of femoral fracture. For this purpose the additional "conical" expansion towards the proximal end is relatively slight, but still sufficient to achieve the desired improvement in stability of the shaft within the femur. To attain this goal without inflicting too much additional stress on the femur, it is particularly advantageous for the overdimensioning to amount to 1-3%; accordingly the maximal height of the additional expansion of the shaft in the proximal region is from ²/₁₀ mm to about ¹⁰/₁₀ mm.

The proposed overdimensioning, specifically in the form of the above-mentioned additional expansion ("cone"), is preferably obtained by an additional coating of the shaft in the proximal region, in particular by means of a plasma coating method employing titanium or hydroxyapatite. It has proved advantageous to build up this coating by applying several layers, in particular a dense, relatively thin base layer and a considerably thicker, porous covering or intermediate layer; where desired, a dense layer of hydroxyapatite can be disposed on the porous intermediate layer.

The point on the length of the shaft at which the additional expansion begins can be the same anteriorly and posteriorly, but can also be different, and the thickening proximal to this point can increase gradually or also take the form of a stepwise increase.

In order to avoid placing too much stress on the femoral bone on one hand, while on the other hand achieving the desired improved fixation of the shaft, it is especially advantageous for the section comprising the additional expansion to have a laterally concave structure in the longitudinal direction (toward the proximal end) and to be shaped approximately like a peaked roof as seen in section perpendicular to the long axis of the shaft.

Another essential aspect consists in a special configuration of the neck of the prosthesis as well, which is flattened in cross section. This cross-sectional shape is to a certain extent matched to that of the flat femur-anchoring section; the spectrum comprises more or less flat ellipses, rectangles rounded in the corner regions, combinations of sections of a circle and straight lines or, in some circumstances, also shapes similar to the shaft cross sections described below, with "peaked-roof-like" side surfaces.

Yet another essential aspect of the invention, particularly advantageous in combination with the proposed additional anterior and/or posterior expansion in the proximal region, consists in providing a differentiated surface structure along the length of the shaft. That is, the distal end of the shaft (in a region extending over about ⅕ of the shaft length) is polished, whereas the remaining region exhibits the usual roughness—achieved in the conventional manner by corundum jets—or is itself divided into two zones. In the latter case the preferred arrangement is an especially rough, open-pored structure in the proximal region, while the middle section of the prosthesis shaft has no open pores and exhibits the above-mentioned intermediate or usual degree of roughness.

Another aspect that should be specially emphasized is that in the proximal region a so-called facet is formed at the boundary between the medial surface and the posterior and anterior surfaces, or between the lateral surface and the posterior and anterior surfaces. The provision of these facets is particularly significant in connection with the overdimensioning of the shaft in the proximal region as proposed here. That is, in the edge regions of the shaft the overdimensioning would be associated with a risk that excessive stress would be imposed on the cortex of the bone, so that it is important to ensure a highly accurate fit here. Therefore the last step in shaping the shaft is to bevel the edge regions down to the precise rasped dimension. It is particularly advantageous for the machined regions to be graded, rounded or additionally beveled towards the side surfaces, as is explained in more detail below.

In a special, advantageous embodiment the cross section of the shaft is approximately trapezoidal in shape, at least in the proximal region; in particular, it has a symmetrical trapezoidal shape with two longer side edges of equal length a, which in cross section delimit the anterior or posterior side surfaces of the shaft, and two shorter side edges that differ in length, of which the shorter corresponds to the medial face and the longer to the lateral face of the shaft.

Additional advantageous structural features and alternatives to the construction in accordance with the invention are described in the subordinate claims and the following exemplary embodiments.

In the following, exemplary embodiments are explained in greater detail with reference to the attached drawings, wherein

BRIEF DESCRIPTION OF THE DRAWINGS

FIG. 10 is a side view of a shaft according to another embodiment, while

DETAILED DESCRIPTION OF THE PREFERRED EMBODIMENT

Figure 1:
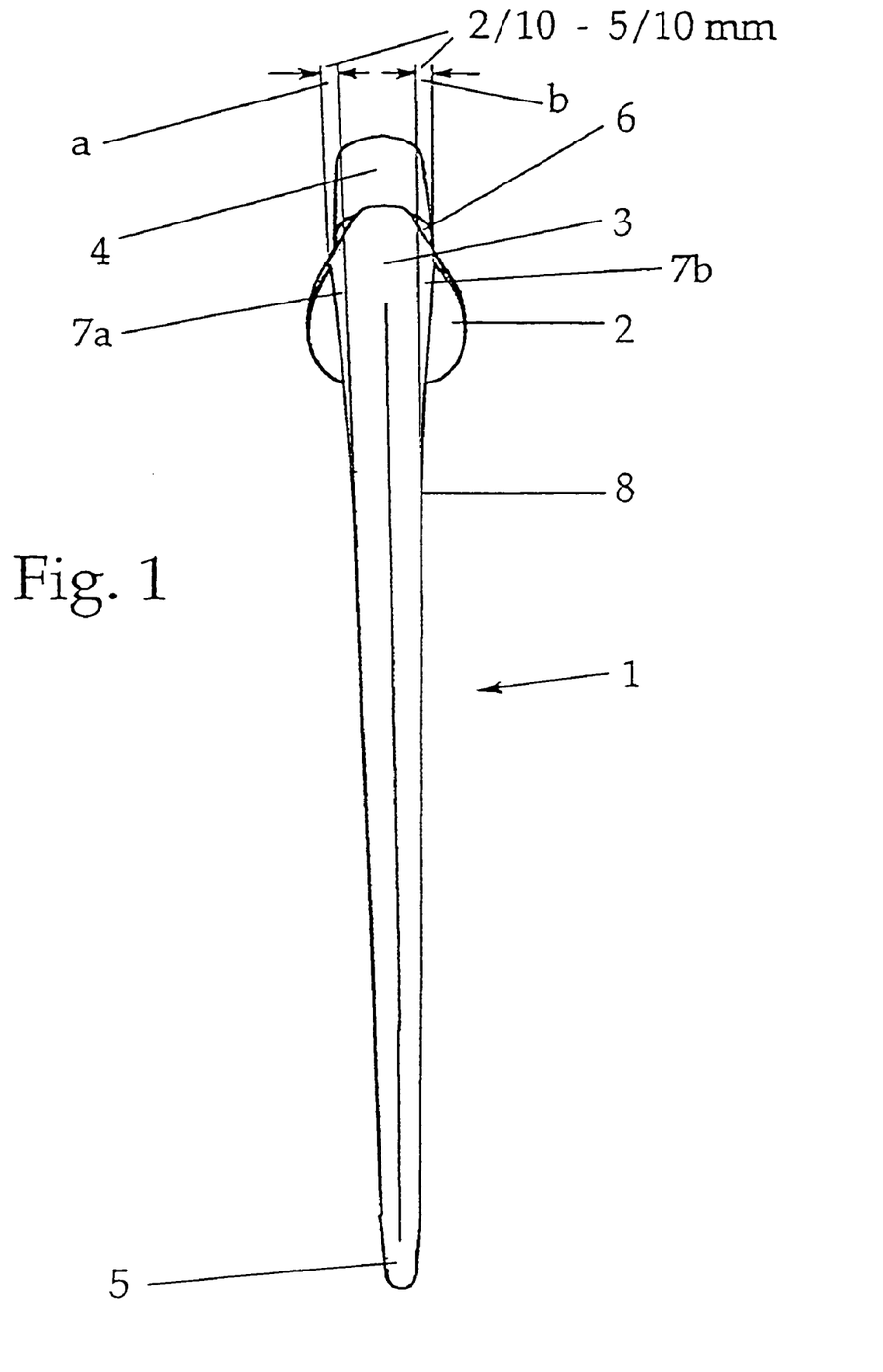
FIG. 1 shows a side face of a shaft according to one embodiment of the invention, as seen from lateral.
Figure 2:
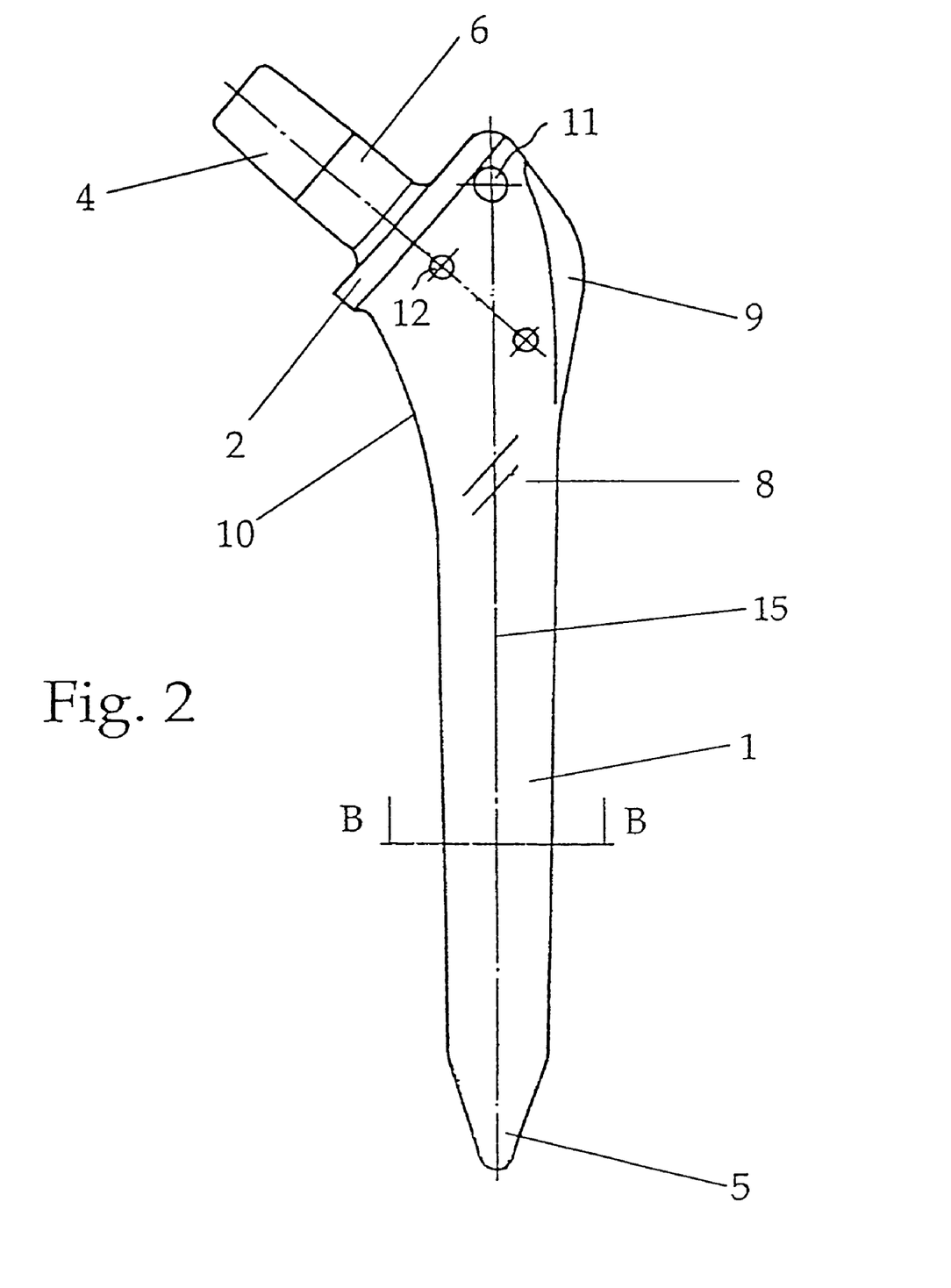
FIG. 2 is a view of the shaft according to FIG. 1 from anterior or posterior.

A shaft 1 shown in FIGS. 1 and 2 serves to anchor a hip-joint prosthesis in the femur. As can be seen in FIGS. 1 and 2, the shaft expands uniformly on all sides in the proximal direction, from the distal end 5 as far as a collar-like projection 2 that separates an anchoring section of the shaft 1 from a prosthesis neck 6. As shown in FIG. 2, proximal to the "cone" the medial narrow side of the shaft is shaped like a continuously curving arch 10, which ends at the above-mentioned projection 2. The reference numeral 3 identifies an upper transition region, the numeral 9 (FIG. 2) a trochanter wing, and the numerals 11 and 12 indicate cross-bores that extend through the shaft from anterior to posterior. These bores have the function of facilitating comparison between X-rays taken at different times. They can also be used to detect a potential displacement of the shaft after it has been in place for a long time. The long axis (longitudinal central axis) of the shaft is identified in FIG. 2 by the reference numeral 15. The above-mentioned conically tapering peg that adjoins the neck 6 of the prosthesis is identified by the numeral 4.

It is evident in FIG. 1 that the shaft 1 at first expands at a constant rate on the anterior and posterior sides, until a proximal region 8 is reached. In the proximal region 8, on the above-mentioned continuous expansion on all sides ("cone") there is superimposed an additional "cone" 7a, 7b on both the anterior and the posterior face; in this region the side surfaces are also modified, for example curve outward. The maximal heights of the additional expansions "a", "b" reach values ranging from ²⁄₁₀ mm to ⁵⁄₁₀ mm. They can have the same configuration on the anterior and posterior surfaces, but it is also conceivable to make the anterior and posterior heights "a" and "b" different from one another.

As mentioned above, experience has shown that the additional expansion 7a, 7b considerably improves the anchoring of the shaft 1 in the proximal region, without causing the femur to be exposed to excessive stress.

Figure 6:
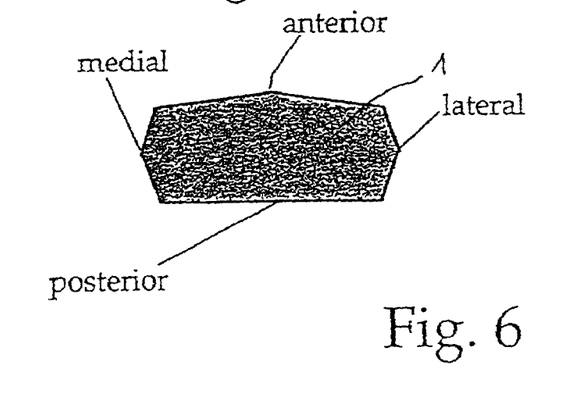
Figure 7:
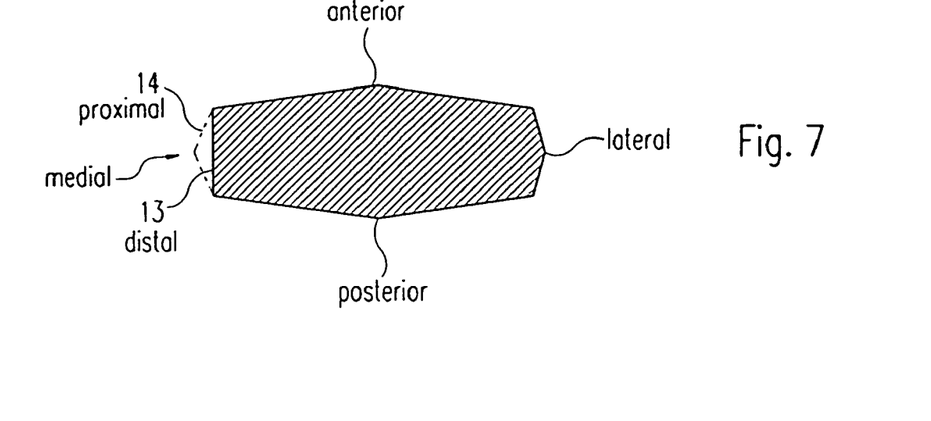
FIGS. 7 and 8 show other alternative cross-sectional shapes of the shaft in accordance with the invention.

As FIGS. 3-8 show very clearly, the shaft 1 in its femur-anchoring section can have different cross-sectional shapes. The shapes of the shaft 1 shown in FIGS. 3-8 represent cross sections at about the level of the line B-B in FIG. 2. These cross-sectional shapes are either the same over the entire length of the shaft, or are present only in the distal or proximal region. In special embodiments, the shaft has a cross section corresponding to FIG. 5 in its distal region, but in the proximal region a cross section corresponding to FIG. 4. In this sense the cross sections according to FIGS. 3-8 can be combined differently depending on the individual situation. FIG. 7 indicates this combination of two different cross sections in a single drawing: the medial side of the shaft 1 is flat in the distal region (medial flat side 13), whereas in the proximal region the medial side gradually changes to a peaked-roof configuration 14.

As has already been mentioned, other cross-section combinations can of course also be selected. For example, as shown in FIG. 6 the posterior side can be flat while the anterior side has a peaked-roof shape. The transition from distal to proximal indicated for the medial side in FIG. 7 can be provided in a similar manner on the posterior and/or anterior surface.

Figures 3, 4, 5:
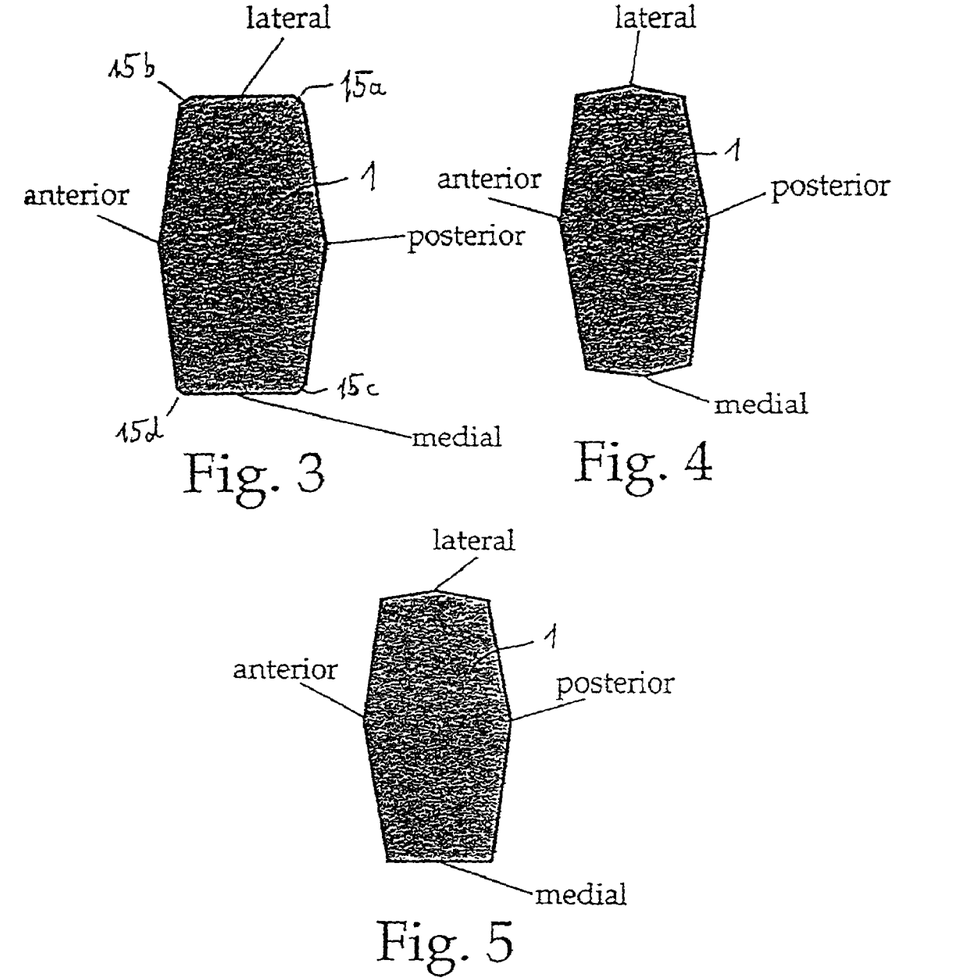
FIGS. 3-6 show embodiments of a shaft constructed in accordance with the invention, in which the cross sections along the line B-B in FIG. 2 have various shapes.
Figure 8:
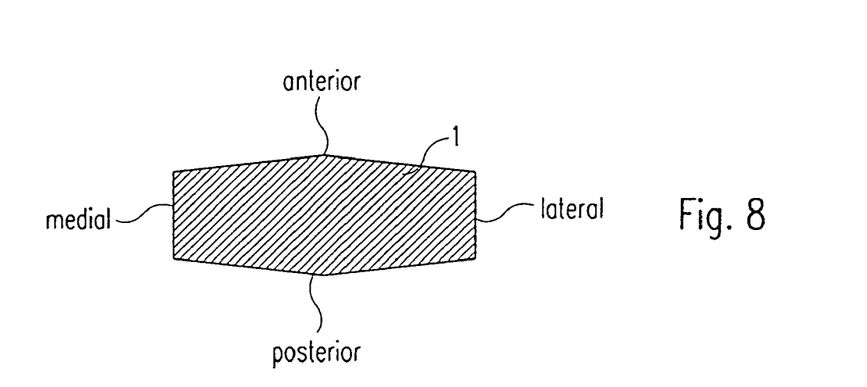

Specifically, the different cross sections shown here can be identified as follows:

FIG. 3: lateral and medial flat
anterior and posterior in the shape of a shallow peaked roof
FIG. 4: lateral, medial, anterior and posterior
each peaked-roof shape
FIG. 5: lateral, anterior and posterior peaked-roof shape
medial flat
FIG. 6: medial, lateral and anterior peaked-roof shape
posterior flat
FIG. 7 anterior, posterior and lateral peaked-roof shape
medial distally flat and proximally peaked-roof shape
FIG. 8: anterior and posterior peaked-roof shape
medial and lateral flat In the embodiment shown in FIG. 3 the corner edges, i.e. the transitional regions between the lateral or medial surfaces and the adjacent anterior and posterior surfaces, are all beveled, i.e. chamfered. The facets thus formed are identified by the reference numerals 15a, 15b, 15c and 15d.

These facets on the one hand cause less risk of damage to the interior of the femur, and on the other hand they also allow the internal cavity to be filled more completely.

The facet angle as a rule is about 45° with respect to the longitudinal midplane oriented parallel to the anterior and posterior surfaces of the shaft 1. This angle can be kept constant over the entire length of the shaft. In an alternative embodiment, within the proximal region this angle becomes gradually less steep from distal to proximal.

Figure 9:
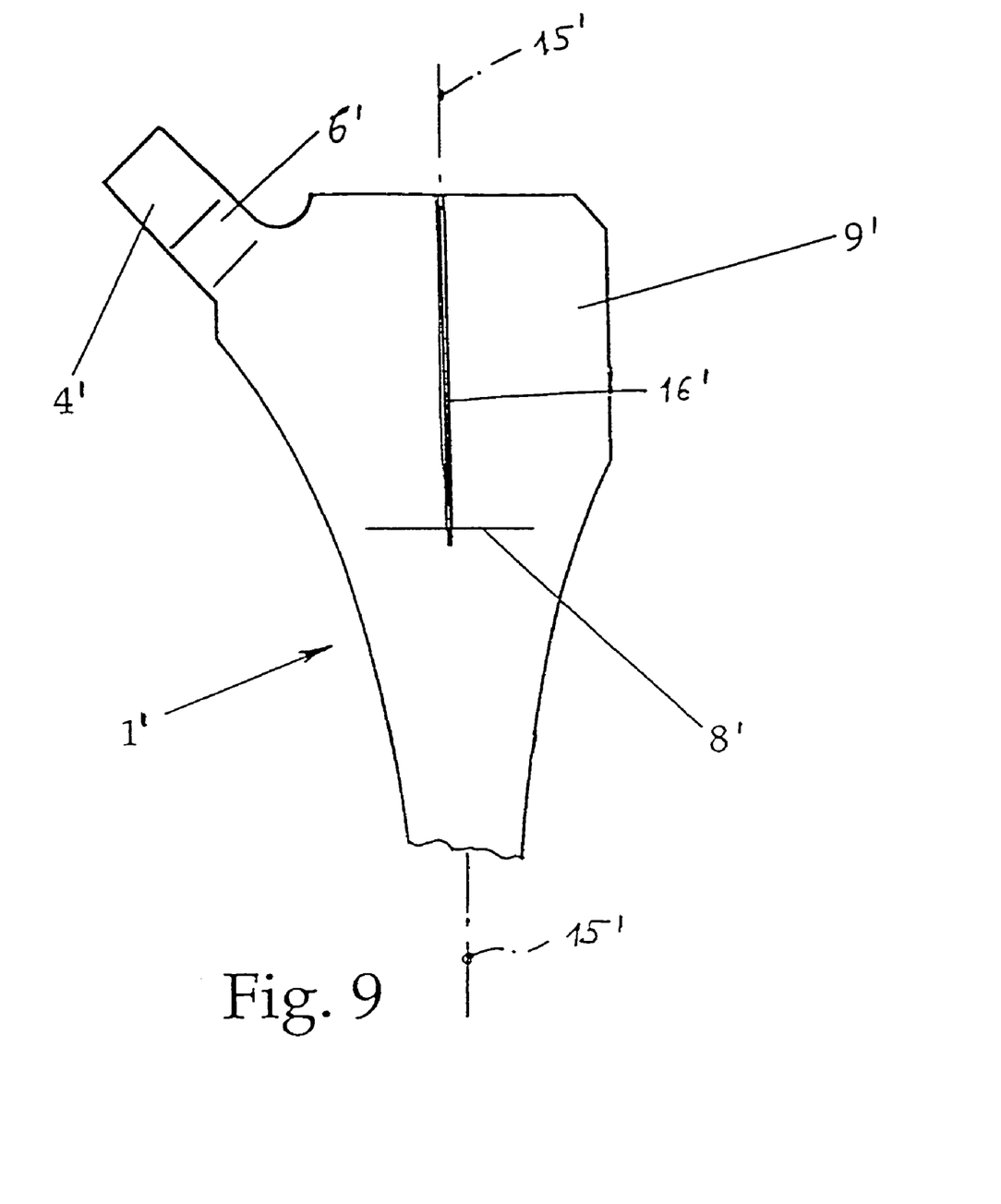
FIG. 9 is a partial side view of another embodiment (proximal region), seen from anterior or posterior.

FIG. 9 shows a modified embodiment of a shaft 1', in the form of a view of the posterior or anterior aspect of only the proximal region. Elements or sections that are the same as those shown in FIG. 1 are identified by the same reference numerals as are used in FIG. 1, and are not explained again in the following.

In this embodiment no collar-like projection between anchoring section and prosthesis neck 6' is provided. This shaft is distinguished by a trochanter wing 9' that is larger than the trochanter wing provided in the shaft according to FIGS. 1 and 2.

The reference numeral 16 identifies a "roof ridge" in the proximal region, which indicates that the proximal region of the shaft, beginning about at the line 8', has the shape of a shallow peaked roof posteriorly and/or anteriorly. Distal to the line 8 the anterior and posterior surfaces of the shaft become planar.

The shaft cross section can be concave or convex on the medial, lateral, posterior and/or anterior side, at least in some regions (for example, by a concave or convex curvature of the surfaces of the "peaked roof").

In another special embodiment the above-mentioned sides of the shaft are provided in at least some regions with longitudinal grooves and/or ridges, each of which in cross section can appear triangular, rectangular or like a peaked roof.

The shaft described here is of course made of a human-compatible material, in particular a titanium alloy. The surfaces can be additionally roughened.

In one preferred embodiment a distal end region of the prosthesis shaft (extending over about one-fifth of the total length) is polished; the adjacent middle region is provided with an intermediate degree of roughness by corundum jets, and the proximal end region has an open-porous structure so that it is particularly rough. In combination with additional expansion in the proximal region, this gradation in surface roughness, by means of which the boundary conditions for growth into the femur are differentiated, achieves a particularly firm anchoring in the proximal region.

In a special variant the additional expansion on the posterior and/or anterior surface of the shaft has no longitudinal concave curvature but instead is made straight. Where there is a concave curvature, instead of conforming to an arc of a circle it can comprise a parabolic, hyperbolic or ellipsoid section. In principle, a convexly curved or S-shaped longitudinal configuration can also be provided.

Figure 10:
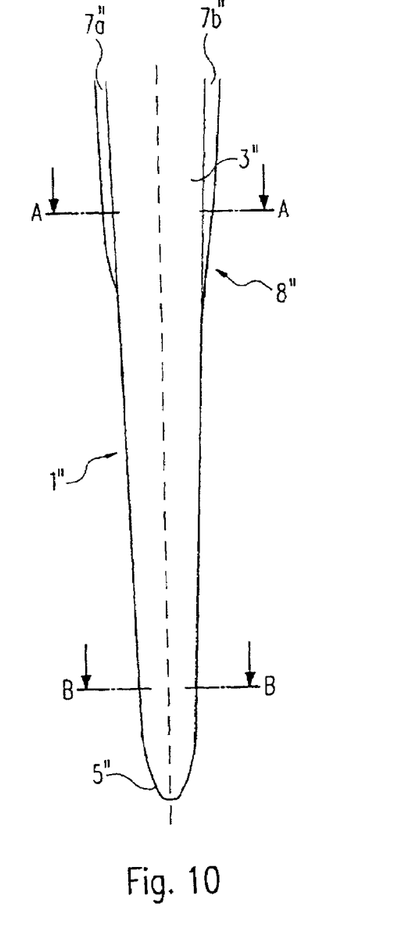

FIG. 10 shows part of another embodiment of a prosthesis shaft 1", which in principle resembles the shafts shown in FIGS. 1, 2 and 9; hence, again, the same reference numerals are used to identify certain elements or regions here as in those figures. The shaft 1" is distinguished, first, by the fact that in its proximal region 8" the anterior and posterior thickenings, 7a" and 7b" respectively, begin at points separated by different distances from the distal end 5" of the shaft. Furthermore, it is evident that proceeding proximally from their points of origin, the thickening 7b" at first expands more gradually than the thickening 7a". These thickenings or expansions 7a", 7b" have a multilayered construction, being formed by a dense base layer ca. 50 μm thick, a porous intermediate layer ca. 300 μm thick, and a dense hydroxyapatite cover layer ca. 50 μm thick (these thickness values are given merely as examples; in order to achieve a particular desired overdimensioning of the shaft in the proximal region, they can vary over a considerable range).

Figure 11:
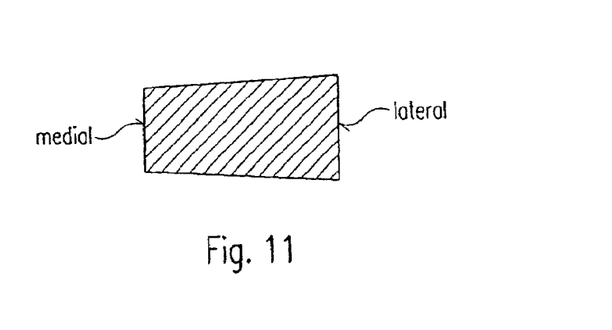
FIGS. 11 and 12 show cross sections of this shaft along the lines A-A and B-B in FIG. 10, respectively.
Figure 12:
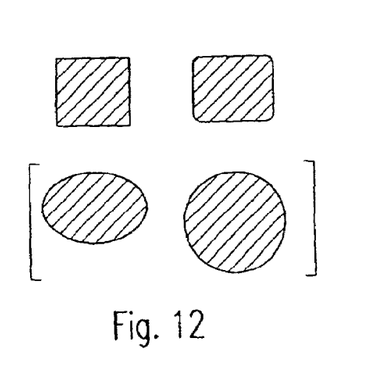

In FIGS. 11 and 12 are shown preferred shaft cross sections along the lines in FIG. 10 identified as A-A and B-B, respectively. The drawing of the shaft cross section in the proximal region, in FIG. 11, is a simplified sketch that takes no account of the added layers; the shape is substantially that of a symmetrical trapezoid, such that the medial face of the shaft, in accordance with the anatomical relationships, is made narrower than the lateral face. In the distal region the shaft cross section (in contrast to the conventional shaft cross sections shown in the lower row of drawings in FIG. 12) can be substantially square or rectangular. The corner edges here, as well as in the case of the trapezoidal cross section in the proximal region, can be rounded or in particular beveled, although this is not shown in FIG. 11 or 12.

Diverse modifications based on the basic trapezoidal shape shown in FIG. 10 are possible: for example, an asymmetrical "X" shape, an "H" with one long and one shorter limb, a "double-H" design with three limbs all of different lengths, a design with concave facets in the edge regions of a trapezoidal cross section, or various hollow profiles with a trapezoidal outer shape.

Figure 13:
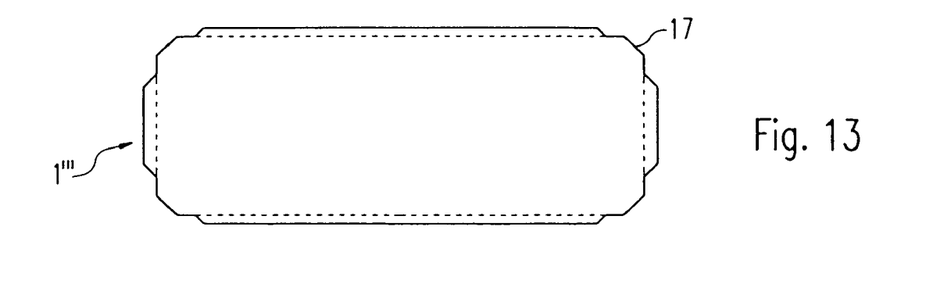
FIGS. 13-17 show various cross-sectional shapes of the prosthesis neck.

To illustrate yet another special embodiment of the anchoring section of a shaft prosthesis 1''' in accordance with the invention, FIG. 13 shows a cross-sectional shape developed from the basic rectangular shape; at all the corner edges it comprises graded chamfer regions 17. The outer contour indicated by the dashed line is a diagrammatic representation of a conventional shaft cross section for similar applications, with corners beveled at a 45° angle with respect to the side surfaces. It can be seen that the new design proposed here (indicated by the continuous line) has dimensions larger than those of this known design over most of each side surface. However, all the chamfered regions include a middle section that is slightly raised so as to coincide with the beveled surfaces of the conventional prosthesis shaft. The outer sections of the chamfered regions are parallel to these surfaces but set slightly further back on both sides, so that the chamfering is graded with respect to the associated side surfaces.

A final beveling to produce the graded edge configuration shown in FIG. 13 has proved to be relatively easy to implement and to have an advantageous effect; in principle, however, there are other possible fine structures in the edge region by means of which the accurate dimensions at the corners (more accurately: the chamfers) can be harmonized with an overdimensioning of the side and end faces. Such structures include, for example, rounding or additional beveled surfaces that are slanted with respect to the main chamfer.

Figure 14:
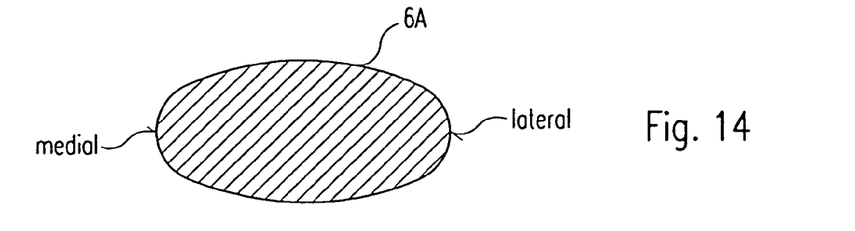
Figure 15:
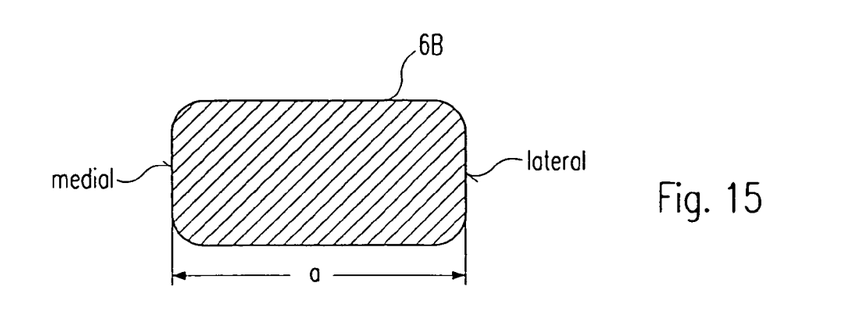
Figure 16:
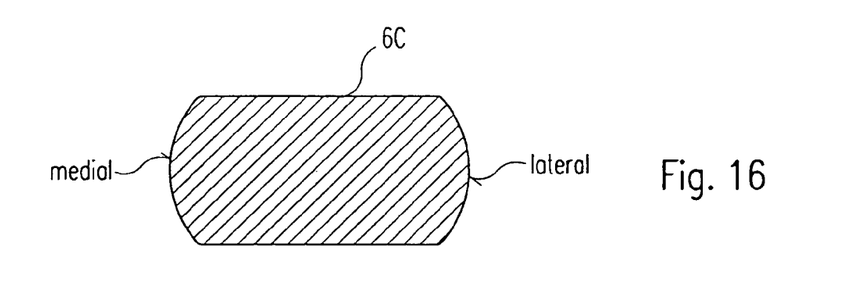

In FIGS. 14-17 are shown in cross section—merely as examples of a large number of possible concrete cross-sectional shapes—some preferred embodiments of the prosthesis neck 3 or 3' of a hip-joint prosthesis as shown in FIGS. 1 and 2 or FIG. 9, respectively. So that they can be distinguished from one another and from the prosthesis necks 6 and 6' according to FIGS. 1 and 9, respectively, the necks in these figures are identified by 6A, 6B, 6C and 6D. In the embodiment according to FIG. 14 the anterior-posterior flattening produces an elliptical cross section, such that the major axis of the ellipse is oriented substantially in the medial-lateral direction. FIG. 15 shows another variant, in which the prosthesis neck has the cross-sectional shape of a rectangle with rounded corners. The rectangle's longer side a here extends—in analogy to the major axis of the ellipse according to FIG. 14—in the medial-lateral direction. In the embodiment shown in FIG. 16 the anterior and posterior boundaries of the cross section are straight lines, whereas the lines bounding it medially and laterally are both parts of a circular arc. The prosthesis neck 6D shown in FIG. 17 has a cross-sectional shape in which all the boundary lines are parts of a circular arc, such that the arcs forming the anterior and posterior boundaries have a radius larger than that of the arcs forming the medial boundary.

Figure 17:
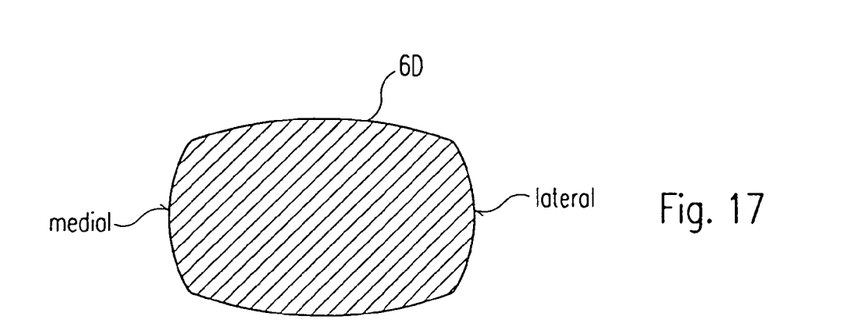

It is easy to see that many mixed forms are possible, intermediate between the various cross-sectional shapes illustrated in FIGS. 14 and 17 and briefly described above; in particular, the curved boundary lines can also be formed by sections of ellipses or parabolas.

All the characteristics disclosed in the application documents are claimed as essential to the invention insofar as they are new to the state of the art individually or in combination.

| List of reference numerals | |
|---|---|
| 1; 1'; 1''; 1''' | Shaft |
| 2 | Collar-like projection |
| 3; 3'; 3'' | Transitional region |
| 4; 4' | Peg |
| 5; 5' | Distal end of shaft |
| 6; 6A; 6B; 6C; 6D | Prosthesis neck |
| 7a, 7b; 7a'', 7b'' | Additional conical expansion anterior/posterior |
| 8; 8'; 8'' | Transition from distal to proximal |
| 9; 9' | Trochanter wing |
| 10 | Arch |
| 11, 12 | Bore |
| 13 | Medial side distally flat |
| 14 | Medial side proximally peaked-roof-shaped |
| 15 | Longitudinal midline of the shaft |
| 15a, 15b, 15c, 15d | Facet |
| 16' | Expansion region |
| 17 | Beveled region |
| a, b | Maximal height of expansion |
| A—A, B—B | Line of section |

The invention claimed is:

1. A shaft of a hip-joint prosthesis for anchoring in a femur, the shaft comprising anterior, posterior, lateral, and medial sides, wherein the shaft is monolithic and expands on all sides from a distal end in the proximal direction and medially merges with a curved section that is continuous with a prosthesis neck, the shaft having a proximal region with an anterior-posterior dimension that is overdimensioned in the range of about 1 to 3%, with respect to a dimension of a cavity formed by a rasp, in such a way that when the shaft is driven in, it compresses the spongy bone tissue over a large area in the proximal region of the femur, said shaft further comprising middle and distal portions dimensioned to substantially exactly match corresponding dimensions of the cavity, wherein the shaft comprises in the proximal region of the shaft an additional thickness that projects outward from a generally planar surface of at least one of the anterior and posterior sides, the additional thickness defining a generally continuous surface on said at least one of the anterior and posterior sides, the generally continuous surface configured to facilitate the press-fitting of the proximal region of the shaft in the femur and inhibit the risk of a femoral fracture, the generally continuous surface comprising at least one dense layer and at least one porous layer having a maximum thickness of between about 2/10 mm and about 1 mm.

2. The shaft according to claim 1, wherein the additional thickness in its longitudinal course exhibits a concave curvature on at least one side.

3. The shaft according to claim 1, wherein the additional thickness runs in a straight line in the direction from distal to proximal on at least one side.

4. The shaft according to claim 1, wherein the additional thickness on the anterior or posterior surface has the shape of a peaked roof as seen in a section perpendicular to the long axis of the shaft.

5. The shaft according to claim 1, wherein the additional thickness on the anterior or posterior surface is constructed at least in some regions so as to have a shallow convex or concave curvature as seen in a section transverse to the long axis of the shaft.

6. The shaft according to claim 4, wherein additional thickness, as seen in a section perpendicular to the long axis of the shaft, on one side—anterior or posterior—has the shape of a peaked roof or is convexly curved, whereas on the other side—posterior or anterior—in at least certain regions it is shaped with a generally pronounced concave curvature.

7. The shaft according to claim 1, wherein at least one of the medial, lateral, anterior, and posterior sides over substantially the entire extent from distal to proximal is substantially continuously constructed in the shape of a peaked roof.

8. The shaft according to claim 5, wherein at least two opposed sides, at least in regions are constructed in the shape of a peaked roof.

9. The shaft according to claim 1, wherein the additional thickness on each of the anterior and posterior sides has a maximal height of about 2/10 mm to about 10/10 mm.

10. The shaft according to claim 1, wherein at least one of the medial and lateral sides is flat in the distal region but has the shape of a peaked roof in the proximal region.

11. The shaft according to claim 1, comprising a peaked-roof configuration on at least one side of the shaft, wherein an angle between sides of the peaked roof changes from distal to proximal.

12. The shaft according to claim 1, wherein the distal region of the shaft is polished along a length of about 1/5 the total length of the shaft.

13. The shaft according to claim 1, further comprising edges at transitional regions between the side surfaces of the shaft, that are beveled at least in the proximal region so as to form longitudinal facets.

14. The shaft according to claim 13, further comprising graded chamfers at the edges in the proximal region, which are beveled so as to conform precisely to corresponding dimensions of the rasp.

15. The shaft according to claim 1, wherein a cross section of the shaft in a plane perpendicular to the long axis has the shape of a trapezoid, such that the side edge of the trapezoid that determines the medial surface of the shaft is shorter than the side edge that determines the lateral surface.

16. The shaft according to claim 1, wherein the additional thickness comprises a coating formed over portions of the shaft.

17. The shaft according to claim 16, wherein the coating has a multilayered construction, which comprises at least one thinner, dense first layer and a thicker, porous second layer disposed thereon.

18. The shaft according to claim 1, wherein the shaft near its distal end has a polished surface and in the remaining region has a rough surface.

19. The shaft according to claim 18, wherein in a proximal region a markedly roughened surface is provided whereas in a middle region there is provided a moderately rough, close-pored surface.

20. The shaft according to claim 8, wherein the at least two opposed sides are constructed in the shape of a peaked roof in the proximal region.

21. The shaft according to claim 9, wherein the additional thickness on each side has a maximal height of 5/10 mm.

22. The shaft according to claim 11, wherein the angle increases continuously from the distal to the proximal ends.

23. The shaft according to claim 1, wherein, in the corner-edge regions of the proximal region of the shaft, the shaft is designed to conform precisely to corresponding dimensions of corner regions of the rasp.

24. The shaft according to claim 14, wherein the graded chamfers are positioned in the middle section of the edges in the proximal region.

25. The shaft according to claim 15, wherein the cross section of the shaft has the shape of a symmetrical trapezoid.

26. The shaft according to claim 16, wherein the coating comprises at least one of Ti and a layer of hydroxyapatite.

27. The shaft according to claim 19, wherein markedly roughened comprises being open-pored.

28. The shaft of claim 1, wherein the additional thickness comprises a separate layer disposed on top of said at least one of the anterior and posterior sides.

29. A flat shaft of a hip-joint prosthesis for anchoring in a femur, the shaft comprising anterior, posterior, lateral, and medial sides, the anterior and posterior sides each defining a planar surface extending substantially along the entire length of the shaft between a distal end and a proximal end of the shaft, wherein the shaft expands substantially continuously on all sides from the distal end to the proximal end and medially merges with a curved section that is continuous with a prosthesis neck, the shaft having a proximal region comprising an additional thickness on the anterior and posterior sides that forms a continuous surface extending outward from the anterior and posterior sides of the shaft, the continuous surface further having a maximum thickness of between about $2/10$ mm and about 1 mm such that an anterior-posterior dimension of the proximal region of the shaft is overdimensioned in the range of about 1 to 3%, with respect to a dimension of a cavity formed by a rasp in cancellous bone, wherein a maximal extent of the prosthesis neck transverse to a long axis thereof is less in the anterior-posterior direction than a maximal extent in the medial-lateral direction.

30. The shaft according to claim 29, wherein the cross section of the prosthesis neck is substantially elliptical or rectangular.

31. The shaft according to claim 29, wherein the cross section of the prosthesis comprises at least one straight and one curved boundary line.

32. A flat shaft of a hip-joint prosthesis adapted to be inserted into a rasped cavity formed at least partially in cancellous bone of a femur, wherein the shaft is contoured to expand substantially continuously in a tapered manner on all sides from a distal end to an opposite proximal end, an anterior surface and a posterior surface of the shaft each defining a planar surface extending substantially along the entire length of the shaft between the distal end and the proximal end, and wherein the shaft medially merges with a curved section that is continuous with a prosthesis neck, the shaft further comprising on at least one of the anterior and posterior surfaces in a proximal region of the shaft an additional thickness having a multilayered structure comprising titanium or hydroxyapatite and comprising at least one dense layer and at least one porous layer so that the dimensions of the shaft are over-dimensioned in an attachment region of the shaft with respect to the dimensions of a cancellous bone portion of the rasped cavity by between about 1 and 3% such that when the shaft is inserted into the femur, the shaft is secured by compression fit within the cancellous bone in the cavity adjacent the proximal end and fits substantially precisely in the cavity adjacent the distal end with minimal compression fit and free-play so as to inhibit movement of the shaft with respect to the femur, wherein the multilayered structure is formed over a base material of the shaft.

33. The shaft of claim 32, wherein the multi-layered structure comprise a dense base layer formed directly over the shaft, and a porous intermediate layer formed directly over the base layer.

34. The shaft of claim 33, wherein the multilayered structure further comprise a dense cover layer formed directly over the intermediate layer.

35. The shaft of claim 34, wherein the base layer is about 50 μm thick, the intermediate layer is about 300 μm thick, and the cover layer is about 50 μm thick.

36. The shaft of claim 34, wherein the cover layer comprises a material selected from the group consisting of hydroxyapatite and titanium.

37. A shaft of a hip-joint prosthesis for anchoring in a femur, the shaft comprising anterior, posterior, lateral, and medial sides, wherein the shaft is monolithic and expands on all sides from a distal end in the proximal direction and medially merges with a curved section that is continuous with a prosthesis neck, the shaft having a proximal region with an anterior-posterior dimension that is overdimensioned in the range of about 1 to 3%, with respect to a dimension of a cavity formed by a rasp, in such a way that when the shaft is driven in, it compresses the spongy bone tissue over a large area in the proximal region of the femur, said shaft further comprising middle and distal portions dimensioned to substantially exactly match corresponding dimensions of the cavity, the proximal region on at least the anterior and posterior side surfaces having an additional thickening on the anterior and posterior side surfaces, wherein the posterior thickening extends along a greater length of the shaft than does the anterior thickening.

38. The shaft according to claim 37, wherein the additional thickening in its longitudinal course exhibits a concave curvature on at least one of the anterior and posterior side surfaces.

39. The shaft according to claim 37, wherein the additional thickening runs in a straight line in the direction from distal to proximal on at least one of the anterior and posterior side surfaces.

40. The shaft according to claim 37, wherein the additional thickening on the anterior or posterior surface has the shape of a peaked roof as seen in cross-section perpendicular to the long axis of the shaft.

41. The shaft according to claim 37, wherein the additional thickening on the anterior or posterior surface is constructed at least in some regions so as to have a shallow convex or concave curvature as seen in a section transverse to the long axis of the shaft.

42. The shaft according to claim 37, wherein the additional thickening on each of the anterior and posterior side surfaces has a maximal height of about $2/10$ mm to about $10/10$ mm.

43. The shaft according to claim 37, wherein the additional thickening comprises a coating formed over portions of the shaft.

44. The shaft according to claim 43, wherein the coating has a multilayered construction, which comprises at least one thinner, dense first layer and a thicker, porous second layer disposed thereon.

45. The shaft of claim 37, wherein the additional thickness comprises a separate layer disposed on top of a generally planar surface of the anterior and posterior sides.

46. A method of implanting a hip joint prosthesis, comprising:
shaping a cavity in an interior of the femur bone, wherein said shaping comprises shaping a proximal attachment region of the cavity in cancellous bone to have dimensions that are smaller than corresponding dimensions of a hip-joint prosthesis shaft configured for insertion into the femur bone, and shaping a distal region of the cavity to have dimensions substantially equal to corresponding dimensions of the shaft; and inserting the shaft into the cavity, the shaft having a distal portion dimensioned to match the dimensions of the distal region of the cavity, the shaft having a proximal portion over-dimensioned by between about 1% and 3% with respect to the proximal attachment region of the cavity so that the proximal portion of the shaft has an additional thickening that compresses spongy bone tissue in the proximal attachment region of the cavity to anchor the shaft in the cavity, and wherein the shaft expands substantially continuously on all sides.

47. The method of claim 46, wherein no portion of the cavity is sized to be larger than the shaft.

48. The method of claim 46, further comprising shaping corner regions of the cavity to match corresponding corner regions of the shaft.

49. The method of claim 46, wherein the shaft is overdimensioned in an anterior-posterior dimension relative to a corresponding anterior posterior dimension of the cavity in the proximal attachment region.

50. The method of claim 49, wherein overdimensioning the anterior posterior dimension of the shaft comprises applying a coating to at least one of an anterior and a posterior side surfaces, the coating having a thickness of between about $2/10$ mm and about 1 mm.

51. The method of claim 50, wherein applying a coating comprises applying at least one dense layer and at least one porous layer.

52. The method of claim 51, wherein the dense layer comprises hydroxyapatite.

* * * * *

UNITED STATES PATENT AND TRADEMARK OFFICE
CERTIFICATE OF CORRECTION

PATENT NO.         : 7,497,875 B1  
APPLICATION NO. : 09/958463  
DATED                 : March 3, 2009  
INVENTOR(S)       : Karl Zweymüller Page 1 of 1

It is certified that error appears in the above-identified patent and that said Letters Patent is hereby corrected as shown below:

On the Title Page

On Page 2, Item 56 under Foreign Patent Documents, please add --*-- to reference

"FR    2 634 642              02/1990".

Signed and Sealed this

First Day of September, 2009

David J. Kappos  
*Director of the United States Patent and Trademark Office*